US005959080A

United States Patent [19]
Payne et al.

[11] Patent Number: 5,959,080
[45] Date of Patent: Sep. 28, 1999

[54] BACILLUS THURINGIENSIS GENES ENCODING NEMATODE-ACTIVE TOXINS

[75] Inventors: Jewel Payne, Davis; Kenneth E. Narva; Jenny Fu, both of San Diego, all of Calif.

[73] Assignee: Mycogen Corporation, San Diego, Calif.

[21] Appl. No.: 09/184,223

[22] Filed: Nov. 2, 1998

Related U.S. Application Data

[63] Continuation of application No. 08/590,554, Mar. 21, 1996, Pat. No. 5,831,011, which is a continuation-in-part of application No. 08/485,568, Jun. 7, 1995, Pat. No. 5,589,382, which is a continuation-in-part of application No. 08/310,197, Sep. 21, 1994, Pat. No. 5,651,965, which is a division of application No. 08/092,155, Jul. 15, 1993, Pat. No. 5,350,577, which is a division of application No. 07/918,345, Jul. 21, 1992, Pat. No. 5,270,448, which is a division of application No. 07/558,738, Jul. 27, 1990, Pat. No. 5,151,363, said application No. 08/590,554, is a continuation-in-part of application No. 08/357,698, Dec. 16, 1994, Pat. No. 5,632,987, which is a division of application No. 08/176,403, Dec. 30, 1993, abandoned, which is a continuation-in-part of application No. 07/999,053, Dec. 31, 1992, abandoned.

[51] Int. Cl.$^6$ .............................. C07K 1/00; C07H 21/04
[52] U.S. Cl. ........................................ 530/350; 536/23.71
[58] Field of Search ........................ 530/350; 536/23.71; 424/96.461

[56] References Cited

U.S. PATENT DOCUMENTS

| | | | |
|---|---|---|---|
| 4,781,922 | 11/1988 | Bone | 424/92 |
| 4,948,734 | 8/1990 | Edwards et al. | 435/252.5 |
| 5,045,314 | 9/1991 | Bone et al. | 424/93 |
| 5,093,120 | 3/1992 | Edwards et al. | 424/93 |
| 5,100,665 | 3/1992 | Hickle et al. | 424/93 L |
| 5,151,363 | 9/1992 | Payne | 435/252.5 |
| 5,270,448 | 12/1993 | Payne | 530/350 |
| 5,350,577 | 9/1994 | Payne | 424/93.461 |

OTHER PUBLICATIONS

Prichard, R.K. et al. (1980) "The Problem of Anthelmintic Resistance in Nematodes" Australian Veterinary Journal 56:239–251.

Coles, G.C. (1986) "Anthelmintic Resistance in Sheep" Veterinary Clinics of North America: Food Animal Practice 2(2):423–432.

Bottjer, K.P., L.W. Bone, S.S. Gill (1985) "Nematoda: Susceptibility of the Egg to Bacillus thuringiensis Toxins" Experimental Parasitology 60:239–244.

Ignoffo, C.M., V.H. Dropkin (1977) "Deleterious Effects of the Thermostable Toxin of Bacillus thuringiensis on Species of Soil–Inhabiting Myceliophagus, and Plant–Parasitic Nematodes" Journal of the Kansas Entomological Society 50(3):394–398.

Ciordia, H., W.E. Bizzell (1961) "A Preliminary Report on the Effects of Bacillus thuringiensis var. thuringiensis Berliner on the Development of the Free–Living Stages of Some Cattle Nematodes" Journal of Parisitology 47:41, abstract No. 86.

Meadows, J. et al. (1990) "Bacillus thuringienes Strains Affect Population Growth of the Free–living Nematode Turbatrix–aceti" Intertebr. Reprod. Dev. 17(1):73–76 (Abstract only).

Meadows, J.R. et al. (1989) "Lethality of Bacillus thuringiensis–morrisoni for Eggs of Trichostronglylus–Colubriformis Nematoda" Invertebr. Reprod. Dev. 15(2):159–161 (Abstract only).

Meadows, J. et al. (1989) "Factors Influencing Lethality of Bacillus thuringiensis–kurstaki toxin for Eggs and Larvae of Trochostrongylus–Colubriformis Nematoda" J. Parasitol 75(2):191–194, (Abstract only).

Bone, L.W. et al. (1987) "Alteration of Trichostronglyus–colubroformis Egg Permeability by Bacillus thurgingiensis–israelensis Toxin" J. Parasitol. 73(2):295–299, (Abstract only).

Primary Examiner—Robert A. Wax
Assistant Examiner—Devesh Srivastava
Attorney, Agent, or Firm—Saliwanchik, Lloyd & Saliwanchik

[57] ABSTRACT

Noven B.t. genes encoding toxins active against nematode pests have been cloned. The DNA encoding the B.t. toxin can be used to transform various hosts to express the B.t. toxin.

3 Claims, 2 Drawing Sheets

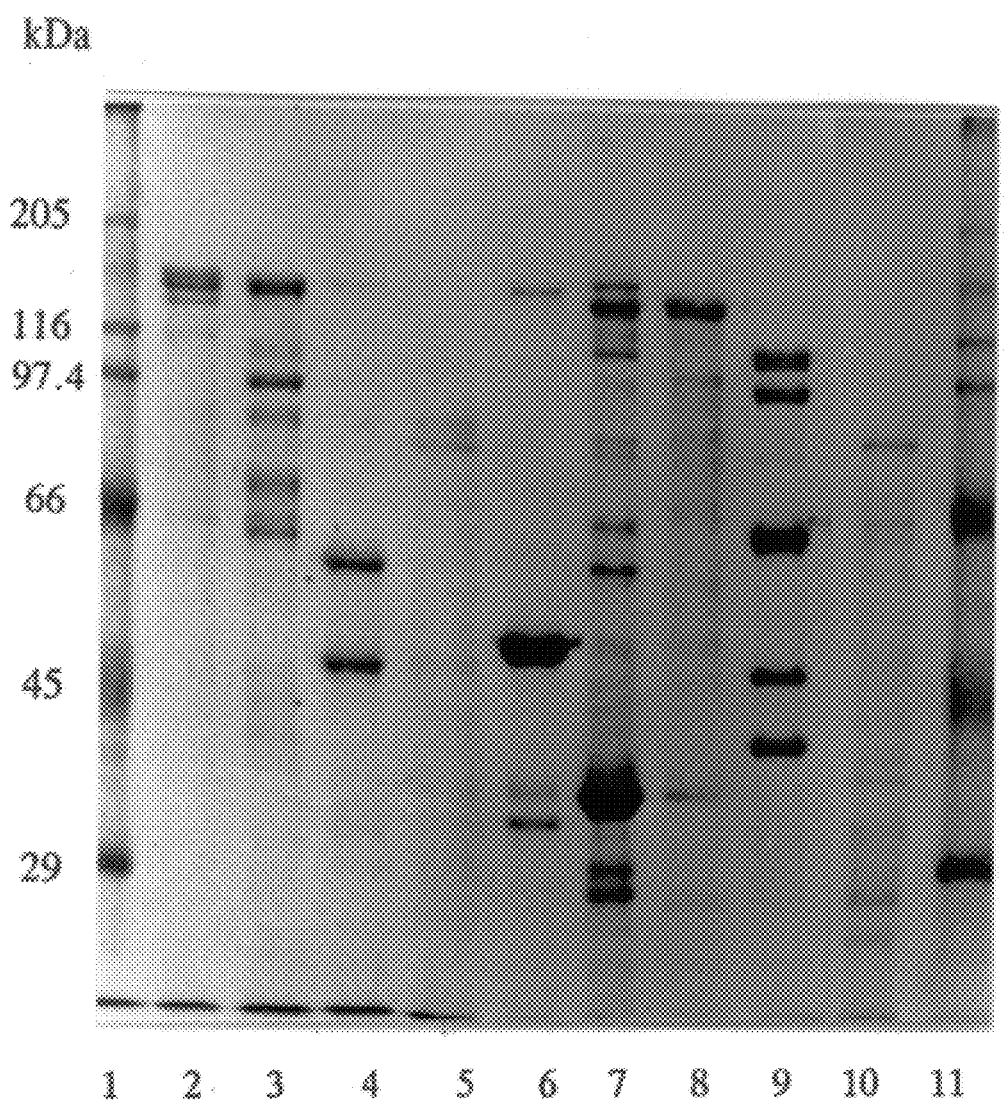

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 23 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:1:

```
GGACCAGGAT TTACAGGWGG RRA                                        23
```

(2) INFORMATION FOR SEQ ID NO:2:

(i) SEQUENCE CHARACTERISTICS:
      (A) LENGTH: 29 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:2:

```
TAACGTGTAT WCGSTTTTAA TTTWGAYTC                                  29
```

(2) INFORMATION FOR SEQ ID NO:3:

(i) SEQUENCE CHARACTERISTICS:
      (A) LENGTH: 3561 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
ATGGATTGTA ATTTACAATC ACAACAAAAT ATTCCTTATA ATGTATTAGC AATACCAGTA    60

TCTAATGTTA ATGCGTTGGT TGATACAGCT GGAGATTTAA AAAAAGCATG GAAGAATTT    120

CAAAAAACTG GTTCTTTTTC ATTAACAGCT TTACAACAAG GATTTTCTGC CTCACAAGGA   180

GGAGCATTCA ATTATTTAAC ATTATTACAA TCAGGAATAT CATTAGCTGG TTCTTTTGTC   240

CCTGGAGGTA CTTTTGTAGC ACCCATTGTT AATATGGTTA TTGGTTGGTT ATGGCCACAT   300

AAAAACAAGA CAGCGGATAC AGAAAATTTA ATAAAATTAA TTGATGAAGA AATTCAAAAA   360

CAATTAAACA AAGCCTTATT AGACCAAGAT AGAAACAATT GGACCTCTTT TTTAGAAAGT   420

ATATTTGATA CTTCAGCTAC AGTAAGTAAT GCAATTATAG ATGCACAGTG GTCAGGTACT   480

GTAGATACTA CAAATAGACA ACAAAAAACT CCAACAACAT CAGATTATCT AAATGTTGTT   540

GGAAAATTTG ATTCAGCGGA TTCTTCAATT ATAACTAATG AAAATCAAAT AATGAATGGC   600

AACTTTGACG TAGCTGCAGC ACCCTATTTT GTTATAGGAG CAACATTACG TCTTTCATTA   660

TATCAATCTT ATATTAAATT TTGTAATAGT TGGATTGATG CAGTTGGATT TAGTACAAAT   720
```

-continued

```
GATGCTAATA CACAAAAAGC TAATTTAGCT CGTACGAAAT TAACTATGCG TACTACAATT    780

AATGAATATA CACAAAGAGT TATGAAAGTT TTTAAAGATT CCAAGAATAT GCCTACAATA    840

GGTACTAATA AATTTAGTGT TGATGCTTAT AATGTATATG TTAAAGGAAT GACATTAAAT    900

GTTTTAGATA TGGTAGCAAT ATGGTCTTCA TTATATCCAA ATGATTATAC TTCACAAACA    960

GCCATAGAAC AAACACGTGT CACTTTTTCA AATATGGTTG ACAAGAAGA AGGTACAGAT    1020

GGAACCCTAA AAATTTACAA TACTTTTGAT TCTCTTAGTT ATCAACATAG CCTAATACCT    1080

AATAATAATG TTAATTTAAT TTCTTATTAT ACTGATGAAT GCAAAATCT AGAATTAGCA    1140

GTATATACTC CTAAAGGTGG AAGTGGATAC GCTTATCCTT ATGGATTTAT TTTAAATTAT    1200

GCAAACAGCA ACTACAAATA TGGTGATAAT GATCCAACAG GCAAACCATT AAATAAACAA    1260

GATGGACCTA TACAACAAT AAATGCAGCA ACTCAAAACA GTAAATATCT AGATGGAGAA    1320

ACAATAAATG GAATAGGGGC ATCCTTACCT GGTTATTGTA CTACAGGATG TTCAGCAACA    1380

GAACAACCTT TTAGTTGTAC TTCTACTGCT AATAGCTATA AGCAAGCTG TAATCCTTCA    1440

GATACTAATC AAAAAATTAA TGCTTTATAT GCTTTTACAC AAACTAATGT AAAGGGAAGC    1500

ACGGGGAAAT TAGGAGTACT GGCAAGTCTT GTTCCATATG ATTTAAATCC TAAAAATGTA    1560

TTTGGTGAAT TAGATTCAGA TACAAATAAT GTTATCTTAA AAGGAATTCC TGCAGAAAAA    1620

GGGTATTTTC CTAATAATGC GCGACCTACT GTTGTAAAAG AATGGATTAA TGGTGCAAGT    1680

GCTGTACCAT TTTATTCAGG AAATACTTTA TTTATGACGG CTACGAATTT AACAGCTACT    1740

CAATATAAAA TTAGAATACG TTATGCAAAT CCAAATTCAG ATACTCAAAT CGGTGTACTA    1800

ATTACGCAAA ATGGTTCTCA AATTTCCAAT AGTAATCTAA CACTTTATAG TACTACTGAT    1860

TCAAGTATGA GTAGTAATTT ACCACAAAAT GTATATGTCA CAGGGGAAAA TGGAAATTAT    1920

ACACTTCTAG ATTTATATAG TACTACTAAT GTTTTATCAA CAGGAGATAT TACATTAAAA    1980

CTTACAGGAG GAAATCAAAA AATATTTATT GATCGAATAG AATTTATTCC TACTATGCCT    2040

GTACCTGCTC CTACTAATAA CACTAATAAC AATAACGGCG ATAACGGCAA TAACAATCCC    2100

CCACACCACG GTTGTGCAAT AGCTGGTACA CAACAACTTT GTTCTGGACC ACCTAAGTTT    2160

GAACAAGTAA GTGATTTAGA AAAAATTACA ACGCAAGTAT ATATGTTATT CAAATCTTCT    2220

TCGTATGAAG AATTAGCTCT AAAAGTTTCT AGCTATCAAA TTAATCAAGT GGCATTGAAA    2280

GTTATGGCAC TATCTGATGA AAAGTTTTGT GAAGAAAAAA GATTGTTACG AAAATTAGTC    2340

AATAAAGCAA ACCAATTACT AGAAGCACGT AACTTACTAG TAGGTGGAAA TTTTGAAACA    2400

ACTCAAAATT GGGTACTTGG AACAAATGCT TATATAAATT ATGATTCGTT TTTATTTAAT    2460

GGAAATTATT TATCCTTACA ACCAGCAAGT GGATTTTTCA CATCTTATGC TTATCAAAAA    2520

ATAGATGAGT CAACATTAAA ACCATATACA CGATATAAAG TTTCTGGATT CATTGGGCAA    2580

AGTAATCAAG TAGAACTTAT TATTTCTCGT TATGGAAAAG AAATTGATAA AATATTAAAT    2640

GTTCCATATG CAGGGCCTCT TCCTATTACT GCTGATGCAT CGATAACTTG TTGTGCACCA    2700

GAAATAGACC AATGTGATGG GGGGCAATCT GATTCTCATT TCTTCAACTA TAGCATCGAT    2760

GTAGGTGCAC TTCACCCAGA ATTAAACCCT GGCATTGAAA TTGGTCTTAA AATTGTGCAA    2820

TCAAATGGTT ATATAACAAT TAGTAATCTA GAAATTATTG AAGAACGTCC ACTTACGAAA    2880

ATGGAAATTC AAGCAGTCAA TCGAAAGAT CACAAATGGA AAGAGAAAA ACTTCTAGAA    2940

TGTGCAAGTG TTAGTGAACT TTTACAACCA ATCATTAATC AAATCGATTC ATTGTTCAAA    3000

GATGCAAACT GGTATAATGA TATTCTTCCT CATGTCACAT ATCAAACTCT AAAAAATATT    3060

ATAGTACCCG ATTTACCAAA ATTAAAACAT TGGTTCATAG ATCATCTCCC AGGTGAATAT    3120
```

```
CATGAAATTG AACAACAAAT GAAAGAAGCT CTAAAACATG CATTTACACA ATTAGACGAG    3180

AAAAATTTAA TCCACAATGG TCACTTTGCA ACTAACTTAA TAGATTGGCA AGTAGAAGGT    3240

GATGCTCGAA TGAAAGTATT AGAAAATAAT GCTTTGGCAT TACAACTTTC CAATTGGGAT    3300

TCTAGTGTTT CACAATCTAT TGATATATTA GAATTTGATG AAGATAAAGC ATATAAACTT    3360

CGCGTATATG CTCAAGGAAG CGGAACAATC CAATTTGGAA ACTGTGAAGA TGAAGCCATC    3420

CAATTTAATA CAAACTCATT CGTATATAAA GAAAAAATAA TCTATTTCGA TACCCCATCA    3480

ATTAACTTAC ACATACAATC AGAAGGTTCT GAATTCGTTG TAAGTAGTAT CGACCTCGTT    3540

GAATTATCAG ACGACGAATA A                                              3561
```

(2) INFORMATION FOR SEQ ID NO:4:

(i) SEQUENCE CHARACTERISTICS:
        (A) LENGTH: 1186 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asp Cys Asn Leu Gln Ser Gln Gln Asn Ile Pro Tyr Asn Val Leu
1               5                   10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270
```

-continued

```
Asp Ser Lys Asn Met Pro Thr Ile Gly Thr Asn Lys Phe Ser Val Asp
    275                 280                 285
Ala Tyr Asn Val Tyr Val Lys Gly Met Thr Leu Asn Val Leu Asp Met
    290                 295                 300
Val Ala Ile Trp Ser Ser Leu Tyr Pro Asn Asp Tyr Thr Ser Gln Thr
305                 310                 315                 320
Ala Ile Glu Gln Thr Arg Val Thr Phe Ser Asn Met Val Gly Gln Glu
                325                 330                 335
Glu Gly Thr Asp Gly Thr Leu Lys Ile Tyr Asn Thr Phe Asp Ser Leu
                340                 345                 350
Ser Tyr Gln His Ser Leu Ile Pro Asn Asn Val Asn Leu Ile Ser
            355                 360                 365
Tyr Tyr Thr Asp Glu Leu Gln Asn Leu Glu Leu Ala Val Tyr Thr Pro
        370                 375                 380
Lys Gly Gly Ser Gly Tyr Ala Tyr Pro Tyr Gly Phe Ile Leu Asn Tyr
385                 390                 395                 400
Ala Asn Ser Asn Tyr Lys Tyr Gly Asp Asn Asp Pro Thr Gly Lys Pro
                405                 410                 415
Leu Asn Lys Gln Asp Gly Pro Ile Gln Gln Ile Asn Ala Ala Thr Gln
                420                 425                 430
Asn Ser Lys Tyr Leu Asp Gly Glu Thr Ile Asn Gly Ile Gly Ala Ser
            435                 440                 445
Leu Pro Gly Tyr Cys Thr Thr Gly Cys Ser Ala Thr Glu Gln Pro Phe
        450                 455                 460
Ser Cys Thr Ser Thr Ala Asn Ser Tyr Lys Ala Ser Cys Asn Pro Ser
465                 470                 475                 480
Asp Thr Asn Gln Lys Ile Asn Ala Leu Tyr Ala Phe Thr Gln Thr Asn
                485                 490                 495
Val Lys Gly Ser Thr Gly Lys Leu Gly Val Leu Ala Ser Leu Val Pro
            500                 505                 510
Tyr Asp Leu Asn Pro Lys Asn Val Phe Gly Glu Leu Asp Ser Asp Thr
        515                 520                 525
Asn Asn Val Ile Leu Lys Gly Ile Pro Ala Glu Lys Gly Tyr Phe Pro
530                 535                 540
Asn Asn Ala Arg Pro Thr Val Val Lys Glu Trp Ile Asn Gly Ala Ser
545                 550                 555                 560
Ala Val Pro Phe Tyr Ser Gly Asn Thr Leu Phe Met Thr Ala Thr Asn
                565                 570                 575
Leu Thr Ala Thr Gln Tyr Lys Ile Arg Ile Arg Tyr Ala Asn Pro Asn
            580                 585                 590
Ser Asp Thr Gln Ile Gly Val Leu Ile Thr Gln Asn Gly Ser Gln Ile
        595                 600                 605
Ser Asn Ser Asn Leu Thr Leu Tyr Ser Thr Thr Asp Ser Ser Met Ser
        610                 615                 620
Ser Asn Leu Pro Gln Asn Val Tyr Val Thr Gly Glu Asn Gly Asn Tyr
625                 630                 635                 640
Thr Leu Leu Asp Leu Tyr Ser Thr Thr Asn Val Leu Ser Thr Gly Asp
                645                 650                 655
Ile Thr Leu Lys Leu Thr Gly Gly Asn Gln Lys Ile Phe Ile Asp Arg
                660                 665                 670
Ile Glu Phe Ile Pro Thr Met Pro Val Pro Ala Pro Thr Asn Asn Thr
            675                 680                 685
Asn Asn Asn Asn Gly Asp Asn Gly Asn Asn Asn Pro Pro His His Gly
```

```
            690                 695                 700
Cys Ala Ile Ala Gly Thr Gln Gln Leu Cys Ser Gly Pro Pro Lys Phe
705                 710                 715                 720
Glu Gln Val Ser Asp Leu Glu Lys Ile Thr Thr Gln Val Tyr Met Leu
                725                 730                 735
Phe Lys Ser Ser Tyr Glu Glu Leu Ala Leu Lys Val Ser Ser Tyr
                740                 745                 750
Gln Ile Asn Gln Val Ala Leu Lys Val Met Ala Leu Ser Asp Glu Lys
                755                 760                 765
Phe Cys Glu Glu Lys Arg Leu Leu Arg Lys Leu Val Asn Lys Ala Asn
770                 775                 780
Gln Leu Leu Glu Ala Arg Asn Leu Leu Val Gly Gly Asn Phe Glu Thr
785                 790                 795                 800
Thr Gln Asn Trp Val Leu Gly Thr Asn Ala Tyr Ile Asn Tyr Asp Ser
                805                 810                 815
Phe Leu Phe Asn Gly Asn Tyr Leu Ser Leu Gln Pro Ala Ser Gly Phe
                820                 825                 830
Phe Thr Ser Tyr Ala Tyr Gln Lys Ile Asp Glu Ser Thr Leu Lys Pro
                835                 840                 845
Tyr Thr Arg Tyr Lys Val Ser Gly Phe Ile Gly Gln Ser Asn Gln Val
850                 855                 860
Glu Leu Ile Ile Ser Arg Tyr Gly Lys Glu Ile Asp Lys Ile Leu Asn
865                 870                 875                 880
Val Pro Tyr Ala Gly Pro Leu Pro Ile Thr Ala Asp Ala Ser Ile Thr
                885                 890                 895
Cys Cys Ala Pro Glu Ile Asp Gln Cys Asp Gly Gly Gln Ser Asp Ser
                900                 905                 910
His Phe Phe Asn Tyr Ser Ile Asp Val Gly Ala Leu His Pro Glu Leu
                915                 920                 925
Asn Pro Gly Ile Glu Ile Gly Leu Lys Ile Val Gln Ser Asn Gly Tyr
                930                 935                 940
Ile Thr Ile Ser Asn Leu Glu Ile Ile Glu Arg Pro Leu Thr Glu
945                 950                 955                 960
Met Glu Ile Gln Ala Val Asn Arg Lys Asp His Lys Trp Lys Arg Glu
                965                 970                 975
Lys Leu Leu Glu Cys Ala Ser Val Ser Glu Leu Leu Gln Pro Ile Ile
                980                 985                 990
Asn Gln Ile Asp Ser Leu Phe Lys Asp Ala Asn Trp Tyr Asn Asp Ile
                995                 1000                1005
Leu Pro His Val Thr Tyr Gln Thr Leu Lys Asn Ile Ile Val Pro Asp
                1010                1015                1020
Leu Pro Lys Leu Lys His Trp Phe Ile Asp His Leu Pro Gly Glu Tyr
1025                1030                1035                1040
His Glu Ile Glu Gln Gln Met Lys Glu Ala Leu Lys His Ala Phe Thr
                1045                1050                1055
Gln Leu Asp Glu Lys Asn Leu Ile His Asn Gly His Phe Ala Thr Asn
                1060                1065                1070
Leu Ile Asp Trp Gln Val Glu Gly Asp Ala Arg Met Lys Val Leu Glu
                1075                1080                1085
Asn Asn Ala Leu Ala Leu Gln Leu Ser Asn Trp Asp Ser Ser Val Ser
                1090                1095                1100
Gln Ser Ile Asp Ile Leu Glu Phe Asp Glu Asp Lys Ala Tyr Lys Leu
1105                1110                1115                1120
```

```
Arg Val Tyr Ala Gln Gly Ser Gly Thr Ile Gln Phe Gly Asn Cys Glu
            1125                1130                1135

Asp Glu Ala Ile Gln Phe Asn Thr Asn Ser Phe Val Tyr Lys Glu Lys
        1140                1145                1150

Ile Ile Tyr Phe Asp Thr Pro Ser Ile Asn Leu His Ile Gln Ser Glu
        1155                1160                1165

Gly Ser Glu Phe Val Val Ser Ser Ile Asp Leu Val Glu Leu Ser Asp
        1170                1175                1180

Asp Glu
1185

(2) INFORMATION FOR SEQ ID NO:5:

(i) SEQUENCE CHARACTERISTICS:
        (A) LENGTH: 3504 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:
```

| | | | | | |
|---|---|---|---|---|---|
| ATGACAAATC | CAACTATACT | ATATCCTAGT | TACCATAATG | TATTAGCTCA | TCCGATTAGA | 60 |
| TTAGATTCTT | TTTTTGATCC | ATTTGTAGAG | ACATTTAAGG | ATTTAAAAGG | GGCTTGGGAA | 120 |
| GAATTCGGAA | AAACGGGATA | TATGGACCCC | TTAAAACAAC | ACCTTCAAAT | CGCATGGGAT | 180 |
| ACTAGTCAAA | ATGAACAGT | GGATTATTTA | GCATTAACAA | AAGCATCTAT | ATCTCTCATA | 240 |
| GGTTTAATTC | CTGGTGCAGA | CGCTGTAGTC | CCTTTTATTA | ATATGTTTGT | AGACTTTATT | 300 |
| TTTCCGAAAT | TATTTGGAAG | AGGTTCTCAA | CAAAATGCTC | AAGCTCAATT | TTTCGAACTA | 360 |
| ATCATAGAAA | AAGTTAAAGA | ACTTGTTGAT | GAAGATTTTA | GAAACTTTAC | CCTTAATAAT | 420 |
| CTACTCAATT | ACCTTGATGG | TATGCAAACA | GCCTTATCAC | ATTTCCAAAA | CGATGTACAA | 480 |
| ATTGCTATTT | GTCAAGGAGA | CAACCAGGA | CTTATGCTAG | ATCAAACACC | AACGGCTTGT | 540 |
| ACTCCTACTA | CAGACCATTT | AATTTCTGTA | AGAGAATCTT | TTAAAGATGC | TCGAACTACA | 600 |
| ATTGAAACAG | CTTTACCACA | TTTTAAAAAT | CCTATGCTAT | CCACAAATGA | TAACACTCCA | 660 |
| GATTTTAATA | GCGACACTGT | CTTATTAACA | TTACCAATGT | ATACAACAGG | AGCGACTTTA | 720 |
| AATCTTATAT | TACATCAAGG | GTATATTCAA | TTCGCAGAAA | GATGGAAATC | TGTAAATTAT | 780 |
| GATGAAAGTT | TTATAAATCA | AACAAAAGTT | GATTTGCAAC | GTCGTATTCA | GGACTATTCT | 840 |
| ACTACTGTAT | CTACCACTTT | TGAAAAATTC | AAACCTACTC | TAAATCCATC | AAATAAAGAA | 900 |
| TCTGTTAATA | AGTATAATAG | ATATGTTCGT | TCCATGACTC | TTCAATCTTT | AGACATTGCT | 960 |
| GCAACATGGC | CTACTTTAGA | TAATGTTAAT | TACCCTTCCA | ATGTAGATAT | TCAATTGGAT | 1020 |
| CAAACTCGCT | TAGTATTTTC | AGATGTTGCA | GGACCTTGGG | AAGGTAATGA | TAATATAACT | 1080 |
| TCGAATATTA | TAGATGTATT | AACACCAATA | AATACAGGGA | TAGGATTTCA | AGAAAGTTCA | 1140 |
| GATCTTAGAA | AATTCACTTA | TCCACGAATA | GAATTACAAA | GCATGCAATT | CCATGGACAA | 1200 |
| TATGTAAACT | CAAAAAGTGT | AGAACATTGT | TATAGCGATG | GTCTTAAATT | AAATTATAAA | 1260 |
| AATAAAACTA | TAACTGCAGG | TGTAAGTAAT | ATTGATGAAA | GTAATCAAAA | TAATAAACAT | 1320 |
| AACTATGGTC | CTGTAATAAA | TAGTCCTATT | ACTGATATCA | ACGTAAATTC | CCAAAATTCT | 1380 |
| CAATATTTAG | ATTTAAATTC | AGTCATGGTA | AATGGTGGTC | AAAAAGTAAC | CGGGTGTTCA | 1440 |
| CCACTTAGTT | CAAATGGTAA | TTCTAATAAT | GCTGCTTTAC | CTAATCAAAA | AATAAATGTT | 1500 |
| ATTTATTCAG | TACAATCAAA | TGATAAACCA | GAAAACATG | CAGACACTTA | TAGAAAATGG | 1560 |

```
GGATATATGA GCAGTCATAT TCCTTATGAT CTTGTTCCAG AAAATGTAAT TGGAGATATA      1620

GATCCGGATA CTAAACAACC GTCATTGCTT CTTAAAGGGT TTCCGGCAGA AAAAGGATAT      1680

GGTGACTCAA TTGCATATGT ATCAGAACCT TTAAATGGTG CGAATGCAGT TAAACTTACT      1740

TCATATCAAG TTCTCCAAAT GGAAGTTACA AATCAAACAA CTCAAAAATA TCGTATTCGC      1800

ATACGTTATG CTACAGGTGG AGATACAGCT GCTTCTATAT GGTTTCATAT TATTGGTCCA      1860

TCTGGAAATG ATTTAACAAA CGAAGGCCAT AACTTCTCTA GTGTATCTTC TAGAAATAAA      1920

ATGTTTGTTC AGGGTAATAA CGGAAAATAT GTATTGAACA TCCTTACAGA TTCAATAGAA      1980

TTACCATCAG GACAACAAAC TATTCTTATT CAAAATACTA ATTCTCAAGA TCTTTTTTTA      2040

GATCGTATTG AATTTATTTC TCTCCCTTCT ACTTCTACTC CTACTTCTAC TAATTTTGTA      2100

GAACCTGAAT CATTAGAAAA GATCATAAAC CAAGTTAATC AATTATTTAG CTCCTCATCT      2160

CAAACTGAAT TGGCTCACAC TGTAAGCGAT TATAAAATTG ATCAAGTAGT GCTAAAAGTA      2220

AATGCCTTAT CCGACGATGT ATTTGGTGTA GAGAAAAAAG CATTACGTAA ACTTGTGAAT      2280

CAGGCCAAAC AACTCAGTAA AGCACGAAAT GTATTGGTCG GTGGAAACTT TGAAAAAGGT      2340

CATGAATGGG CACTAAGCCG TGAAGCAACA ATGGTCGCAA ATCATGAGTT ATTCAAAGGG      2400

GATCATTTAT TATTACCACC ACCAACCCTA TATCCATCGT ATGCATATCA AAAAATTGAT      2460

GAATCGAAAT TAAAATCCAA TACACGTTAT ACTGTTTCCG GCTTTATTGC GCAAAGTGAA      2520

CATCTAGAAG TCGTTGTGTC TCGATACGGG AAAGAAGTAC ATGACATGTT AGATATCCCG      2580

TATGAAGAAG CCTTACCAAT TTCTTCTGAT GAGAGTCCAA ATTGTTGCAA ACCAGCTGCT      2640

TGTCAGTGTT CATCTTGTGA TGGTAGTCAA TCAGATTCTC ATTTCTTTAG CTATAGTATC      2700

GATGTTGGTT CCCTACAATC AGATGTAAAT CTCGGCATTG AATTCGGTCT TCGTATTGCG      2760

AAACCAAACG GATTTGCGAA AATCAGTAAT CTAGAAATTA AGAAGATCG TCCATTAACA       2820

GAAAAGAAA TCAAAAAAGT ACAACGTAAA GAACAAAAAT GGAAAAAAGC ATTTAACCAA       2880

GAACAAGCCG AAGTAGCGAC AACACTCCAA CCAACGTTAG ATCAAATCAA TGCTTTGTAT      2940

CAAAATGAAG ATTGGAACGG TTCCGTTCAC CCGGCCAGTG ACTATCAACA TCTGTCCGCT      3000

GTTGTTGTAC AACGTTACC AAAACAAAGA CATTGGTTTA TGGAGGGTCG AGAAGGCGAA       3060

CATGTTGTTC TGACGCAACA ATTCCAACAA GCATTGGATC GTGCGTTCCA ACAAATCGAA      3120

GAACAAAACT TAATCCACAA TGGTAATTTG GCGAATGGAT TAACAGATTG GACTGTCACA      3180

GGAGATGCAC AACTTACGAT CTTTGACGAA GATCCAGTAT TAGAACTAGC GCATTGGGAT      3240

GCAAGTATCT CTCAAACCAT TGAAATTATG GATTTTGAAG GAAGACACAG AATACAAACT      3300

GCGTGTACGT GGAAAAGGCA AAGGAACAGT TACCGTTCAA CATGGAGGAA GAGATTAGAA      3360

ACGATGACAT TCAATACAAC GAGTTTTACA ACACAAGAAC AAACCTTCTA CTTCGAAGGA      3420

GATACAGTGG ACGTACATGT TCAATCAGAG AATAACACAT TCCTGATAGA TAGTGTGGAA      3480

CTCATTGAAA TCATAGAAGA GTAA                                             3504
```

(2) INFORMATION FOR SEQ ID NO:6:

(i) SEQUENCE CHARACTERISTICS:
        (A) LENGTH: 1167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Thr Asn Pro Thr Ile Leu Tyr Pro Ser Tyr His Asn Val Leu Ala

```
  1                   5                    10                   15
His Pro Ile Arg Leu Asp Ser Phe Phe Asp Pro Phe Val Glu Thr Phe
                20                   25                   30
Lys Asp Leu Lys Gly Ala Trp Glu Glu Phe Gly Lys Thr Gly Tyr Met
            35                   40                   45
Asp Pro Leu Lys Gln His Leu Gln Ile Ala Trp Asp Thr Ser Gln Asn
        50                   55                   60
Gly Thr Val Asp Tyr Leu Ala Leu Thr Lys Ala Ser Ile Ser Leu Ile
65                   70                   75                   80
Gly Leu Ile Pro Gly Ala Asp Ala Val Val Pro Phe Ile Asn Met Phe
                85                   90                   95
Val Asp Phe Ile Phe Pro Lys Leu Phe Gly Arg Gly Ser Gln Gln Asn
                100                  105                  110
Ala Gln Ala Gln Phe Phe Glu Leu Ile Ile Glu Lys Val Lys Glu Leu
            115                  120                  125
Val Asp Glu Asp Phe Arg Asn Phe Thr Leu Asn Asn Leu Leu Asn Tyr
        130                  135                  140
Leu Asp Gly Met Gln Thr Ala Leu Ser His Phe Gln Asn Asp Val Gln
145                  150                  155                  160
Ile Ala Ile Cys Gln Gly Glu Gln Pro Gly Leu Met Leu Asp Gln Thr
                165                  170                  175
Pro Thr Ala Cys Thr Pro Thr Thr Asp His Leu Ile Ser Val Arg Glu
                180                  185                  190
Ser Phe Lys Asp Ala Arg Thr Thr Ile Glu Thr Ala Leu Pro His Phe
            195                  200                  205
Lys Asn Pro Met Leu Ser Thr Asn Asp Asn Thr Pro Asp Phe Asn Ser
        210                  215                  220
Asp Thr Val Leu Leu Thr Leu Pro Met Tyr Thr Thr Gly Ala Thr Leu
225                  230                  235                  240
Asn Leu Ile Leu His Gln Gly Tyr Ile Gln Phe Ala Glu Arg Trp Lys
                245                  250                  255
Ser Val Asn Tyr Asp Glu Ser Phe Ile Asn Gln Thr Lys Val Asp Leu
                260                  265                  270
Gln Arg Arg Ile Gln Asp Tyr Ser Thr Thr Val Ser Thr Thr Phe Glu
            275                  280                  285
Lys Phe Lys Pro Thr Leu Asn Pro Ser Asn Lys Glu Ser Val Asn Lys
        290                  295                  300
Tyr Asn Arg Tyr Val Arg Ser Met Thr Leu Gln Ser Leu Asp Ile Ala
305                  310                  315                  320
Ala Thr Trp Pro Thr Leu Asp Asn Val Asn Tyr Pro Ser Asn Val Asp
                325                  330                  335
Ile Gln Leu Asp Gln Thr Arg Leu Val Phe Ser Asp Val Ala Gly Pro
            340                  345                  350
Trp Glu Gly Asn Asp Asn Ile Thr Ser Asn Ile Ile Asp Val Leu Thr
        355                  360                  365
Pro Ile Asn Thr Gly Ile Gly Phe Gln Glu Ser Asp Leu Arg Lys
            370                  375                  380
Phe Thr Tyr Pro Arg Ile Glu Leu Gln Ser Met Gln Phe His Gly Gln
385                  390                  395                  400
Tyr Val Asn Ser Lys Ser Val Glu His Cys Tyr Ser Asp Gly Leu Lys
            405                  410                  415
Leu Asn Tyr Lys Asn Lys Thr Ile Thr Ala Gly Val Ser Asn Ile Asp
        420                  425                  430
```

-continued

```
Glu  Ser  Asn  Gln  Asn  Asn  Lys  His  Asn  Tyr  Gly  Pro  Val  Ile  Asn  Ser
          435                 440                 445

Pro  Ile  Thr  Asp  Ile  Asn  Val  Asn  Ser  Gln  Asn  Ser  Gln  Tyr  Leu  Asp
     450                 455                 460

Leu  Asn  Ser  Val  Met  Val  Asn  Gly  Gly  Gln  Lys  Val  Thr  Gly  Cys  Ser
465                 470                 475                           480

Pro  Leu  Ser  Ser  Asn  Gly  Asn  Ser  Asn  Ala  Ala  Leu  Pro  Asn  Gln
               485                 490                      495

Lys  Ile  Asn  Val  Ile  Tyr  Ser  Val  Gln  Ser  Asn  Asp  Lys  Pro  Glu  Lys
               500                 505                 510

His  Ala  Asp  Thr  Tyr  Arg  Lys  Trp  Gly  Tyr  Met  Ser  Ser  His  Ile  Pro
          515                 520                 525

Tyr  Asp  Leu  Val  Pro  Glu  Asn  Val  Ile  Gly  Asp  Ile  Asp  Pro  Asp  Thr
     530                 535                 540

Lys  Gln  Pro  Ser  Leu  Leu  Lys  Gly  Phe  Pro  Ala  Glu  Lys  Gly  Tyr
545                 550                 555                      560

Gly  Asp  Ser  Ile  Ala  Tyr  Val  Ser  Glu  Pro  Leu  Asn  Gly  Ala  Asn  Ala
               565                 570                 575

Val  Lys  Leu  Thr  Ser  Tyr  Gln  Val  Leu  Gln  Met  Glu  Val  Thr  Asn  Gln
               580                 585                 590

Thr  Thr  Gln  Lys  Tyr  Arg  Ile  Arg  Ile  Arg  Tyr  Ala  Thr  Gly  Gly  Asp
               595                 600                 605

Thr  Ala  Ala  Ser  Ile  Trp  Phe  His  Ile  Ile  Gly  Pro  Ser  Gly  Asn  Asp
     610                 615                 620

Leu  Thr  Asn  Glu  Gly  His  Asn  Phe  Ser  Ser  Val  Ser  Ser  Arg  Asn  Lys
625                 630                 635                           640

Met  Phe  Val  Gln  Gly  Asn  Asn  Gly  Lys  Tyr  Val  Leu  Asn  Ile  Leu  Thr
               645                 650                 655

Asp  Ser  Ile  Glu  Leu  Pro  Ser  Gly  Gln  Gln  Thr  Ile  Leu  Ile  Gln  Asn
               660                 665                 670

Thr  Asn  Ser  Gln  Asp  Leu  Phe  Leu  Asp  Arg  Ile  Glu  Phe  Ile  Ser  Leu
               675                 680                 685

Pro  Ser  Thr  Ser  Thr  Pro  Thr  Ser  Thr  Asn  Phe  Val  Glu  Pro  Glu  Ser
     690                 695                 700

Leu  Glu  Lys  Ile  Ile  Asn  Gln  Val  Asn  Gln  Leu  Phe  Ser  Ser  Ser  Ser
705                 710                 715                           720

Gln  Thr  Glu  Leu  Ala  His  Thr  Val  Ser  Asp  Tyr  Lys  Ile  Asp  Gln  Val
               725                 730                 735

Val  Leu  Lys  Val  Asn  Ala  Leu  Ser  Asp  Asp  Val  Phe  Gly  Val  Glu  Lys
               740                 745                 750

Lys  Ala  Leu  Arg  Lys  Leu  Val  Asn  Gln  Ala  Lys  Gln  Leu  Ser  Lys  Ala
     755                 760                 765

Arg  Asn  Val  Leu  Val  Gly  Gly  Asn  Phe  Glu  Lys  Gly  His  Glu  Trp  Ala
     770                 775                 780

Leu  Ser  Arg  Glu  Ala  Thr  Met  Val  Ala  Asn  His  Glu  Leu  Phe  Lys  Gly
785                 790                 795                           800

Asp  His  Leu  Leu  Leu  Pro  Pro  Thr  Leu  Tyr  Pro  Ser  Tyr  Ala  Tyr
                    805                 810                 815

Gln  Lys  Ile  Asp  Glu  Ser  Lys  Leu  Lys  Ser  Asn  Thr  Arg  Tyr  Thr  Val
               820                 825                 830

Ser  Gly  Phe  Ile  Ala  Gln  Ser  Glu  His  Leu  Glu  Val  Val  Val  Ser  Arg
               835                 840                 845

Tyr  Gly  Lys  Glu  Val  His  Asp  Met  Leu  Asp  Ile  Pro  Tyr  Glu  Glu  Ala
850                 855                 860
```

-continued

```
Leu Pro Ile Ser Ser Asp Glu Ser Pro Asn Cys Cys Lys Pro Ala Ala
865                 870                 875                 880

Cys Gln Cys Ser Ser Cys Asp Gly Ser Gln Ser Asp Ser His Phe Phe
                885                 890                 895

Ser Tyr Ser Ile Asp Val Gly Ser Leu Gln Ser Asp Val Asn Leu Gly
                900                 905                 910

Ile Glu Phe Gly Leu Arg Ile Ala Lys Pro Asn Gly Phe Ala Lys Ile
            915                 920                 925

Ser Asn Leu Glu Ile Lys Glu Asp Arg Pro Leu Thr Glu Lys Glu Ile
            930                 935                 940

Lys Lys Val Gln Arg Lys Glu Gln Lys Trp Lys Lys Ala Phe Asn Gln
945                 950                 955                 960

Glu Gln Ala Glu Val Ala Thr Thr Leu Gln Pro Thr Leu Asp Gln Ile
                965                 970                 975

Asn Ala Leu Tyr Gln Asn Glu Asp Trp Asn Gly Ser Val His Pro Ala
                980                 985                 990

Ser Asp Tyr Gln His Leu Ser Ala Val Val Pro Thr Leu Pro Lys
                995                 1000                1005

Gln Arg His Trp Phe Met Glu Gly Arg Glu Gly His Val Val Leu
        1010                1015                1020

Thr Gln Gln Phe Gln Gln Ala Leu Asp Arg Ala Phe Gln Gln Ile Glu
1025                1030                1035                1040

Glu Gln Asn Leu Ile His Asn Gly Asn Leu Ala Asn Gly Leu Thr Asp
                1045                1050                1055

Trp Thr Val Thr Gly Asp Ala Gln Leu Thr Ile Phe Asp Glu Asp Pro
                1060                1065                1070

Val Leu Glu Leu Ala His Trp Asp Ala Ser Ile Ser Gln Thr Ile Glu
        1075                1080                1085

Ile Met Asp Phe Glu Gly Arg His Arg Ile Gln Thr Ala Cys Thr Trp
        1090                1095                1100

Lys Arg Gln Arg Asn Ser Tyr Arg Ser Thr Trp Arg Lys Arg Leu Glu
1105                1110                1115                1120

Thr Met Thr Phe Asn Thr Thr Ser Phe Thr Thr Gln Glu Gln Thr Phe
                1125                1130                1135

Tyr Phe Glu Gly Asp Thr Val Asp Val His Val Gln Ser Glu Asn Asn
                1140                1145                1150

Thr Phe Leu Ile Asp Ser Val Glu Leu Ile Glu Ile Glu Glu
                1155                1160                1165
```

BACILLUS THURINGIENSIS GENES ENCODING NEMATODE-ACTIVE TOXINS

CROSS-REFERENCE TO RELATED APPLICATIONS

This application is a continuation of application Ser. No. 08/590,554, filed Mar. 21, 1996 (now U.S. Pat. No. 5,831,011); which is a continuation-in-part of application Ser. No. 08/485,568, filed Jun. 7, 1995, now U.S. Pat. No. 5,589,382; which is a continuation-in-part of application Ser. No. 08/310,197, filed Sep. 21, 1994, now U.S. Pat. No. 5,651,965; which is a division of Ser. No. 08/092,155, filed Jul. 15, 1993, now U.S. Pat. No. 5,350,577; which is a division of Ser. No. 07/918,345, filed Jul. 21, 1992, now U.S. Pat. No. 5,270,448; which is a division of 07/558,738, filed Jul. 27, 1990, now U.S. Pat. No. 5,151,363. Application Ser. No. 08/590,554 is also a continuation-in-part of application Ser. No. 08/357,698, filed Dec. 16, 1994, now U.S. Pat. No. 5,632,987; which is a division of Ser. No. 08/176,403, filed Dec. 30, 1993, now abandoned; which is a continuation-in-part of 07/999,053, filed Dec. 31, 1992, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner and Kim, 1988). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* var. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. *israelensis* and *B.t.* var. *tenebrionis* (a.k.a. *M*-7, a.k.a. *B.t.* var. *san diego*), have been used commercially to control insects of the orders Diptera and Coleoptera, respectively (Gaertner, 1989). See also Couch, 1980 and Beegle, 1978. Krieg et al., 1983, describe *Bacillus thuringiensis* var. *tenebrionis*, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte and Whiteley, 1989). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

The cloning and expression of a *B.t.* crystal protein gene in *Escherichia coli* has been described in the published literature (Schnepf and Whiteley, 1981). U.S. Pat. No. 4,448,885 and U.S. Pat. No. 4,467,036 both disclose the expression of *B.t.* crystal proteins in *E. coli*. U.S. Pat. Nos. 4,797,276 and 4,853,331 disclose *B. thuringiensis* var. *tenebrionis* (a.k.a. *B.t. san diego*, a.k.a. *M*-7) which can be used to control coleopteran pests in various environments. U.S. Pat. No. 4,918,006 discloses *Bacillus thuringiensis* var. *israelensis* toxins which are active against dipteran pests. This patent reports that a protein of about 27 kD, and fragments thereof, are responsible for the dipteran activity. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes.

The accepted methodology for control of nematodes has centered around the use of the drug benzimidazole and its congeners. The use of these drugs on a wide scale has led to many instances of resistance among nematode populations (Prichard et al., 1980; Coles, 1986). There are more than 100,000 described species of nematodes.

A small number of research articles have been published concerning the effects of δ-endotoxins from *B. thuringiensis* species on the viability of nematode eggs. Bottjer et al. (1985) have reported that *B.t. kurstaki* and *B.t. israelensis* were toxic in vitro to eggs of the nematode *Trichostrongylus colubriformis*. In addition, 28 other *B.t.* strains were tested with widely variable toxicities. The most potent had $LD_{50}$ values in the nanogram range. Ignoffo and Dropkin (1977) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, Ciordia and Bizzell (1961) gave a preliminary report on the effects of *B. thuringiensis* on some cattle nematodes.

At the present time there is a need to have more effective means to control the many nematodes that cause considerable damage to susceptible hosts. Effective means would advantageously employ biological agents, such as *B.t.* pesticides. As a result of extensive research and investment of resources, many other patents have issued for new *B.t.* isolates and new uses of *B.t.* isolates. However, the discovery of new *B.t.* isolates and new uses of known *B.t.* isolates remains an empirical, unpredictable art.

BRIEF SUMMARY OF THE INVENTION

The subject invention concerns novel δ-endotoxin genes obtainable from *B.t.* isolates PS167P, PS80JJ1, PS158D5, PS169E, PS177F1, PS177G, PS204G4, and PS204G6, wherein the genes encode proteins which are active against nematode pests. These toxin genes can be transferred to suitable hosts as described herein.

Further aspects of the subject invention concern nematode-active toxins, and fragments thereof, encoded by the genes disclosed herein. Another embodiment of the subject invention concerns hosts transformed with the genes of the subject invention. In a preferred embodiment, the transformed hosts are plants.

BRIEF DESCRIPTION OF THE DRAWINGS

FIG. 1 is a photograph of 9% SDS polyacrylamide gel electrophoresis showing alkali-soluble proteins of nematode active strains.

FIG. 1B: Lane(1) Protein standard,(2) PS17,(3) PS33F2, (4) PS52A1,(5) PS63B,(6), PS69D1,(7) PS169E,(8) PS167P,(9) PS204G4,(10) PS158D5,(11) Protein standard.

BRIEF DESCRIPTION OF THE SEQUENCES

Figure 1A:
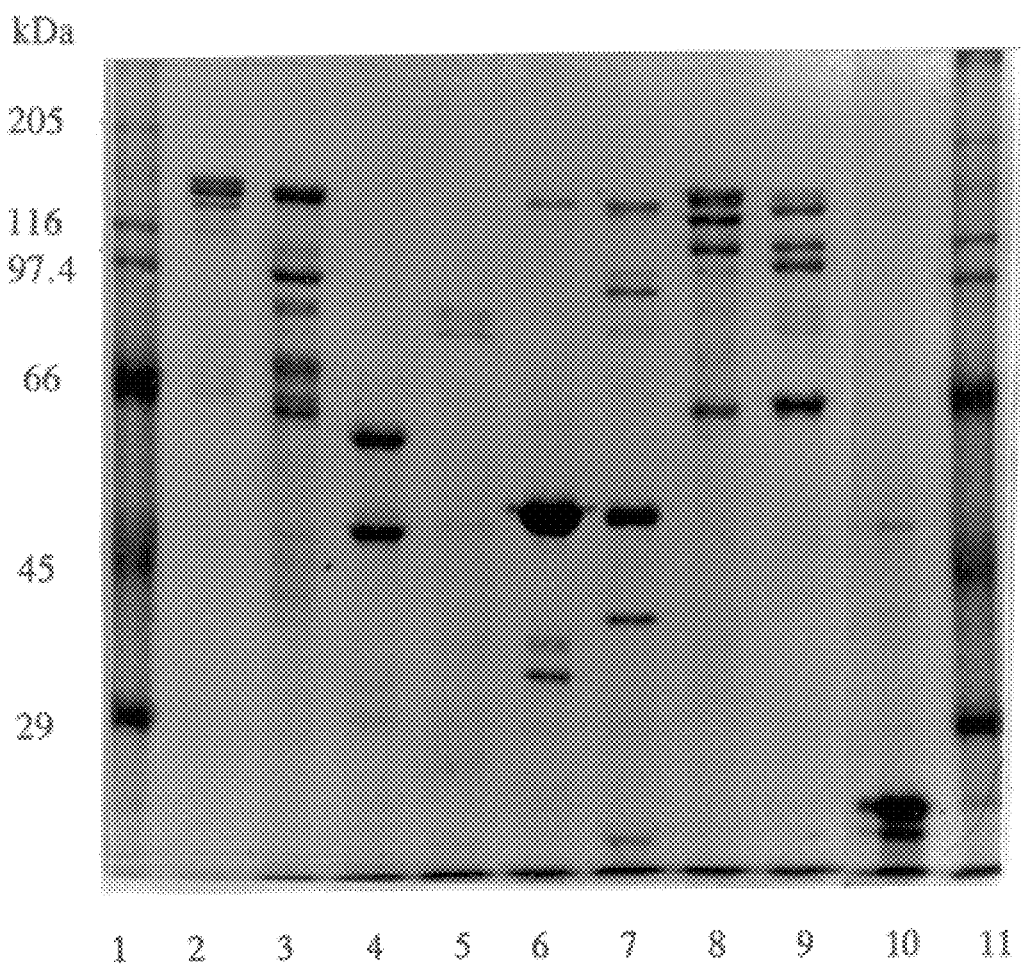
FIG. 1A: Lane(1) Protein standard,(2) PS17,(3) PS33F2, (4) PS52A1,(5) PS63B,(6), PS69D1,(7) PS80JJ1,(8) PS177F1,(9) PS177G,(10) PS204G6,(11) Protein standard.

SEQ ID NO.1 is the nucleotide sequence of a "forward" oligonucleotide primer used for PCR amplification of the 80JJ1 and 167P genes.

SEQ ID NO.2 is the nucleotide sequence of a "reverse" oligonucleotide primer used for PCR amplification of the 80JJ1 and 167P genes.

SEQ ID NO.3 is the nucleotide sequence of the 80JJ1 toxin gene.

SEQ ID NO.4 is the amino acid sequence of the 80JJ1 protein.

SEQ ID NO.5 is the nucleotide sequence of the 167P toxin gene.

SEQ ID NO.6 is the amino acid sequence of the 167P protein.

DETAILED DISCLOSURE OF THE INVENTION

The subject invention pertains to novel genes which encode nematode-active toxins. The toxins themselves are also an important aspect of the invention. A further embodiment of the subject invention is the transformation of suitable hosts to confer upon these hosts the ability to express nematode-active toxins.

The *Bacillus thuringiensis* isolates from which the genes of the subject invention can be obtained have been deposited in the permanent collection of the Agricultural Research Service Patent Culture Collection (NRRL), Northern Regional Research Center, 1915 North University Street, Peoria, Ill. 61604, USA. The accession numbers are as follows:

| Culture | Repository No. | Deposit Date |
| --- | --- | --- |
| B.t. strain PS80JJ1 | NRRL B-18679 | July 17, 1990 |
| B.t. strain PS158D5 | NRRL B-18680 | July 17, 1990 |
| B.t. strain PS167P | NRRL B-18681 | July 17, 1990 |
| B.t. strain PS169E | NRRL B-18682 | July 17, 1990 |
| B.t. strain PS177F1 | NRRL B-18683 | July 17, 1990 |
| B.t. strain PS177G | NRRL B-18684 | July 17, 1990 |
| B.t. strain PS204G4 | NRRL B-18685 | July 17, 1990 |
| B.t. strain PS204G6 | NRRL B-18686 | July 17, 1990 |
| E. coli NM522(pMYC2379) | NRRL B-21155 | November 3, 1993 |
| E. coli NM522(pMYC2382) | NRRL B-21329 | September 28, 1994 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified. In some instances, the fusion protein may contain, in addition to the characteristic pesticidal activity of the toxins specifically exemplified, another pesticidal activity contributed by the fusion process. As used herein, the terms "variants" or "variations" of genes refer to nucleotide sequences which encode the same toxins or which encode equivalent toxins having similar pesticidal activity. As used herein, the term "equivalent toxins" refers to toxins having the same or essentially the same biological activity against the target pests as the claimed toxins.

It should be apparent to a person skilled in this art that genes encoding nematode-active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" amino acid sequence refers to sequences which have amino acid substitutions, deletions, additions, or insertions which do not materially affect the pesticidal activity of the protein.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions.

Following is a table which provides characteristics of certain isolates useful according to the subject invention.

TABLE 2

Description of B.t. strains toxic to nematodes

| Culture | Crystal Description | Approx. MW (kDa) | Serotype | NRRL Deposit | Deposit Date |
| --- | --- | --- | --- | --- | --- |
| PS80JJ1 | multiple attached | 130, 90, 47, 37 | 4a4b, sotto | B-18679 | 7-17-90 |
| PS158D5 | attached amorphic | 80 | novel | B-18680 | 7-17-90 |
| PS167P | attached amorphic | 120 | novel | B-18681 | 7-17-90 |
| PS169E | attached amorphic | 150, 128, 33 | non-motile | B-18682 | 7-17-90 |
| PS177F1 | multiple attached | 140, 116, 103, 62 | non-motile | B-18683 | 7-17-90 |
| PS177G | multiple attached | 135, 125, 107,98,62 | non-motile | B-18684 | 7-17-90 |
| PS204G4 | multiple attached | 105, 98, 90, 60, 44, 37 | non-motile | B-18685 | 7-17-90 |
| PS204G6 | long amorphic | 23, 21 | wuhanensis | B-18686 | 7-17-90 |

N.D. = not determined

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested by the pest. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of pests. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, e.g., genera Metarhizium, Bavaria, Saccharomyces, Cryptococcus, Kluyveromyces, Sporobolomyces, Rhodotorula, and Aureobasidium. Of particular interest are such bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of nematodes using the isolates, toxins, and genes of the subject invention can be accomplished by a variety of methods known to those skilled in the art. These methods include, for example, the application of *B.t.* isolates to the pests (or their location), the application of recombinant microbes to the pests (or their locations), and the transformation of plants with genes which encode the pesticidal toxins of the subject invention. Recombinant microbes may be, for example, a *B.t., E. coli,* or Pseudomonas. Transformations can be made by those skilled in the art using standard techniques. Materials necessary for these transformations are disclosed herein or are otherwise readily available to the skilled artisan. For example, the gene encoding the 167P toxin is provided herein as SEQ ID NO.5. The deduced amino acid sequence for the 167P toxin is provided in SEQ ID NO.6.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art and are used with commercial strains of *B. thuringiensis* (HD-1) active against Lepidoptera, e.g., caterpillars. The *B.t.* isolates (spores and crystals) of the subject invention can be used to control nematode pests.

The *B.t.* toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the nematode-active agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the nematode-active agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

In addition to having anthelminthic activity within the digestive tract of mammals, spores from nematicidal B.t. isolates will pass through the animals' digestive tract, germinate and multiply in the feces, and thereby provide additional control of nematode larva which hatch and multiply therein.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematode pests, e.g., plants, soil, or water by spraying, dusting, sprinkling, or the like.

Mutants. Mutants of the B.t. isolates of the subject invention can be made by procedures well known in the art. For example, an asporogenous mutant can be obtained through ethylmethane sulfonate (EMS) mutagenesis. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1—Culturing B.t. Strains

A subculture of a B.t. strain can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |

-continued

| Salts Solution (100 ml) | |
|---|---|
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2—Activity of *Bacillus thuringiensis* Isolates Against *Panagrellus redivivus*

Worms were collected in a tube and allowed to settle for about 15 minutes. The water was decanted and replaced with fresh water three or four times until the water remained clear. 250 μl rinsed nematodes (20–30 worms), and 100 μl of a spore/crystal suspension were added to 650 μl water in each well of a multi-well tray. Nematodes were counted and the numbers recorded. After four days, the live worms were counted and percent mortality calculated.

TABLE 3

Bioassay results

| U.S. Pat. No. 4,948,734 | Mortality |
|---|---|
| *B.t.* strain No. | |
| PS17 | 90% |
| PS33F2 | 30% |
| PS52A1 | 100% |
| PS63B | 92% |
| PS69D1 | 100% |
| Novel *B.t.* strain No. | |
| PS80JJ1 | 99% |
| PS158D5 | 99% |
| PS167P | 96% |
| PS169E | 100% |
| PS177F1 | 96% |
| PS177G | 100% |
| PS204G4 | 100% |
| PS204G6 | 100% |
| Control | 0% |

Tables 4 and 5 show the molecular mass of the alkali-soluble proteins in each novel nematode-active strain, as compared to previously known *B.t.* strains.

TABLE 4

Previously known nematode-active strains

| *B.t.* Strain | Approximate Molecular Mass of Proteins (kDa) |
|---|---|
| PS17 | 155, 145, 135 |
| PS33F2 | 140, 94, 86, 68, 65, 62 |
| PS52A1 | 57, 45 |
| PS63B | 84, 82, 78 |
| PS69D1 | 135, 46, 32 |

TABLE 5

New Nematode-Active Strains

| Novel *B.t.* Strain | Approximate Molecular Mass of Proteins (kDa) |
|---|---|
| PS80JJ1 | 130, 90, 47, 37 |
| PS158D5 | 80 |
| PS167P | 120 |
| PS169E | 150, 128, 33 |
| PS177F1 | 140, 116, 103, 62 |
| PS177G | 135, 125, 107, 98, 62 |
| PS204G4 | 105, 98, 90, 60, 44, 37 |
| PS204G6 | 23, 21 |

EXAMPLE 3—Cloning and Expression of a of Novel Toxin Gene from *Bacillus thuringiensis* Strain PS80JJ1

Total cellular DNA was prepared from *Bacillus thuringiensis* (*B.t.* ) cells grown to an optical density, at 600 nm, of 1.0. Cells were pelleted by centrifugation and resuspended in protoplast buffer (20 mg/ml lysozyme in 0.3 M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lystate was extracted twice with phenol:chloroform (1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An approximately 700–800 bp DNA fragment from a novel PS80JJ1 130 kDa toxin gene was obtained by polymerase chain reaction (PCR) amplification using PS80JJ1 cellular DNA and the following primers:

```
"Forward": 5' GGACCAGGATTTACAGG(TA)GG(AG)(AG)A 3'          (SEQ ID NO. 1)

"Reverse": 5' TAACGTGTAT(AT)CG(CG)TTTTAATTT(TA)GA(CT)TC 3'.  (SEQ ID NO. 2)
```

The DNA fragment was cloned into pBluescript S/K (Stratagene, LaJolla, Calif.) and partially sequenced by dideoxynucleotide DNA sequencing methodology (Sanger et al., 1977) using Sequenase (US Biochemicals, Cleveland, Ohio). DNA sequences unique to at least one PS80JJ1 toxin gene were identified by computer comparison with other known δ-endotoxin genes.

The 700–800 bp DNA fragment was radiolabelled with $^{32}$P and used in standard hybridizations of Southern blots of PS80JJ1 total cellular DNA. Hybridizing bands included an approximately 1.8 kbp EcoRI fragment and an approximately 9.5 kbp HindIII fragment. These hybridizing DNA bands contain toxin genes or restriction fragments of toxin genes from PS80JJ1.

A gene library was constructed from PS80JJ1 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with the probe described above. Hybridizing phage were plaque-purified and used to infect liquid cultures of *E. coli* KW251 cells for isolation of DNA by standard procedures (Maniatis et al.).

For subcloning the gene encoding the PS80JJ1 130 kDa toxin, preparative amounts of phage DNA were digested with XhoI and electrophoresed on an agarose gel. The approximately 12 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident *B.t.* plasmid [Lereclus et al. ]). The ligation mix was used to transform frozen, competent *E. coli* NM522 cells (ATCC 47000). β-galactosidase-transformants were screened by restriction digestion of alkaline lysate plasmid minipreps as above. The desired plasmid construct, pMYC2379, contains a toxin gene that is novel compared to other toxin genes containing insecticidal proteins.

The PS80JJ1 toxin gene encoded by pMYC2379 was sequenced using the ABI373 automated sequencing system and associated software. Sequence analysis of the toxin gene revealed that it encodes a protein of approximately 130,000 daltons, deduced from the DNA sequence. The nucleotide and deduced amino acid sequences are shown in SEQ ID NOS. 3 and 4, respectively.

pMYC2379 was introduced into the acrystalliferous (Cry$^-$) *B.t.* host, CryB (A. Aronson, Purdue University, West Lafayette, Ind.), by electroporation. Expression of the 130 kDa toxin was demonstrated by SDS-PAGE analysis.

A subculture of *E. coli* NM522 containing plasmid pMYC2379 was deposited in the permanent collection of the Patent Culture Collection (NRRL), Regional Research Center, 1815 North University Street, Peoria, Ill. 61604 USA or Nov. 3, 1991. The accession number is NRRL B-21155.

EXAMPLE 4—Cloning and Expression of a Novel Toxin Gene from *Bacillus thuringiensis* PS167P Total cellular DNA was prepared as in Example 3.

An approximately 700–800 bp DNA fragment from novel PS167P 130 kDa toxin genes was obtained by polymerase chain reaction (PCR) amplification using PS167P cellular DNA and SEQ ID NOS. 1 and 2. This DNA fragment was cloned into pBluescript S/K (Stratagene, La Jolla, Calif.) and partially sequenced by dideoxynucleotide DNA sequencing methodology (Sanger et al., 1977) using Sequenase (U.S. Biochemicals, Cleveland, Ohio). DNA sequences unique to at least two PS167P toxin genes were identified by computer comparison with other known δ-endotoxin genes.

The 700–800 bp DNA fragment was radiolabelled with $^{32}$P and used in standard hybridizations of Southern blots of PS167P total cellular DNA. Hybridizing bands included approximately 1.8 kbp and 2.3 kbp EcoRI fragments and approximately 5.5 kbp and 8.0 kbp HindIII fragments. These DNA fragments contain toxin genes or restriction fragments of toxin genes unique to PS167P.

A gene library was constructed from PS167P DNA partially digested with NdeII. Partial restriction digests were fractionated by agarose gel electrophoresis. DNA fragments 9.3 to 23 kbp in size were excised from gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with the probe described above. Hybridizing phage were plaque-purified and used to infect liquid cultures of *E. coli* KW251 cells for isolation of DNA by standard procedures (Maniatis et al, 1989).

Southern blot analysis revealed that one of the recombinant phage isolates contained an approximately 5 kbp SalI band that hybridized to the PS167P toxin gene probe. One of the SalI sites flanking the PS167P toxin gene resides in the phage vector DNA sequence, while the other flanking SalI site is located within the PS167P DNA insert. This SalI fragment was subcloned by standard methods into pBluescript S/K (Stratagene, San Diego, Calif.) for DNA sequence analysis. The DNA insert was subcloned further as a SacI-KpnI fragment into pHTBlueII (an *E. coli/B. thuringiensis* shuttle vector comprised of pBluescript S/K and the replication origin from a resident *B.t.* plasmid [Lereclus et al., 1989] to yield pMYC2382. To test expression of the PS167P toxin gene in *B.t.* , pMYC2382 was introduced into the acrystalliferous (Cry-) *B.t.* host, CryB (A. Aronson, Purdue University, West Lafayette, Ind.) by electroporation. Expression of the approximately 130 kDa PS167P toxin encoded by pMYC2382 was demonstrated by SDS-PAGE analysis.

The PS167P toxin gene encoded by pMYC2382 was sequenced using the ABI373 automated sequencing system and associated software. The PS167P toxin nucleotide (SEQ ID NO.5) and deduced amino acid (SEQ ID NO.6) sequences are novel compared to other toxin genes encoding pesticidal proteins.

A subculture of *E. coli* NM522 containing plasmid pMYC2382 was deposited in the permanent collection of the Patent Culture Collection (NRRL), Regional Research Center, 1815 North University Street, Peoria, Ill. 61604 USA on Sep. 28, 1994. The accession number is NRRL B-21329.

EXAMPLE 5—Insertion of Toxin Genes Into Plants

One aspect of the subject invention is the transformation of plants with genes encoding a toxin active against nematode pests. The transformed plants are resistant to attack by nematodes.

Genes encoding pesticidal toxins, as disclosed herein, can be modified for optimum expression in plant, linked to a plant selectable marker gene, and inserted into a genome of plant cell using a variety of techniques which are well known to those skilled in the art. Any plant may be used in accordance with this invention, including angiosperms, gymnosperms, monocotyledons and dicotyledons. Preferred plants include soybean, sunflower, cotton, potato, alfalfa, maize, rice and wheat. The transformation method itself is not critical to the invention but may include transformation with T-DNA using *Agrobacterium tumefaciens* or *A. rhizogenes* as the transformation agent, liposome fusion, microinjection, microprojectile bombardment, chemical agent (PEG or calcium chloride)-assisted DNA uptake, or electroporation, as well as other possible methods. Reference may be made to the literature for full details of the known methods, especially Holsters et al., 1978; Fromm et al., 1985; Horsch et al., 1985; Herrera-Estrella et al., 1983; Crossway et al., 1986; Lin, 1966; and Steinkiss and Stabel, 1983.

Use of a plant selectable marker in transformation allows for selection of transformed cells rather than cells that do not contain the inserted DNA. Various markers exist for use in plant cells and generally provide resistance to a biocide or antibiotic, including but not limited to, kanamycin, G418, hygromycin, and phosphinothricin. Visual markers including but not limited to b-glucuronidase, b-galactosidase, B-peru protein, green fluorescent protein, and luciferase may also be used. After transformation, those cells that have the DNA insert can be selected for by growth in a defined medium and assayed for marker expression, whether by resistance or visualization. Cells containing the DNA insert can be regenerated into plants. As long as stably transformed plants are obtained, the method used for regeneration will depend on the plant tissue and transformation method used and is not critical to the invention. However, for example, where cell suspensions have been used for transformation, transformed cells can be induced to produce calli and the calli subsequently induced to form shoots, which may then be transferred to an appropriate nutrient medium to regenerate plants. Alternatively, explants such as hypocotyl tissue or embryos may be transformed and regenerated by shoot induction in the appropriate media, followed by root and whole plant formation. Whatever regeneration method is used, the result will be stably transformed plants that can vegetatively and sexually transmit the transformed trait(s) to progeny, so that, if necessary, the transformed plant can be crossed with untransformed plants in order to transfer the trait to more appropriate germplasm for breeding purposes.

EXAMPLE 6—Cloning of Novel *B.t.* Genes Into Insect Viruses

A number of viruses are known to infect insects. These viruses include, for example, baculoviruses and entomopoxviruses. In one embodiment of the subject invention, nematode-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (1990) and Martens et al. (1990).

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Patents

U.S. Pat. No. 4,448,885.
U.S. Pat. No. 4,467,036.
U.S. Pat. No. 4,695,455
U.S. Pat. No. 4,695,462.
U.S. Pat. No. 4,797,276.
U.S. Pat. No. 4,849,217.
U.S. Pat. No. 4,853,331.
U.S. Pat. No. 4,918,006.
U.S. Pat. No. 4,948,734.
U.S. Pat. No. 5,135,867.
U.S. Pat. No. 5,151,363.

Foreign Patent Documents

EP 120 516.

Other References

An et al. (1985) *EMBO J.* 4:277–287.

Beegle, C. C., (1978) "Use of Entomogenous Bacteria in Agroecosystems," *Developments in Industrial Microbiology* 20:97–104.

Bottjer, Bone, and Gill (1985) *Experimental Parasitology* 60:239–244.

Ciordia, H., W. E. Bizzell (1961) *Jour. of Parasitology* 47:41 [abstract].

Coles, G. C. (1986) "Anthelmintic resistance in sheep," In *Veterinary Clinics of North America: Food Animal Practice,* Vol 2:423–432 (Herd, R. P., eds.) W. B. Saunders, New York.

Couch, T. L. (1980) "Mosquito Pathogenicity of *Bacillus thuringiensis* var. *israelensis," Developments in Industrial Microbiology* 22:61–76.

Feitelson, J. S., J. Payne, L. Kim (1992) *Bio/Technology* 10:271–275.

Fraley et al. (1985) *Crit. Rev. Plant Sci.* 4:1–46.

Gaertner, F. H. (1989) "Cellular Delivery Systems for Insecticidal Proteins: Living and Non-Living Microorganisms," in *Controlled Delivery of Crop Protection Agents,* R. M. Wilkins, ed., Taylor and Francis, New York and London, 1990, pp. 245–255.

Gaertner, F. H., L. Kim (1988) *TIBTECH* 6:S4–S7.

Hoekema (1985) In: *The Binary Plant Vector System,* Offset-durkkerij Kanters B. V., Alblasserdam, Chapter 5.

Höfte, H., H. R. Whiteley (1989) *Microbiological Reviews* 52(2):242–255.

Holsters et al. (1978) *Mol. Gen. Genet.* 163:181–187.

Humason, Gretchen L., *Animal Tissue Techniques,* W. H. Freeman and Company, 1967.

Ignoffo, C. M. and Dropkin, V. H. (1977) *J. Kans. Entomol. Soc.* 50:394–398.

Krieg, A., A. M. Huger, G. A. Langenbruch, W. Schnetter (1983) *Z. ang. Ent.* 96:500–508.

Lereclus, D. et al. (1989) *FEMS Microbiology Letters* 60:211–218.

Maniatis, T., E. F. Fritsch, J. Sambrook (1982) *Molecular Cloning: A Laboratory Manual,* Cold Spring Harbor Laboratory, Cold Spring Harbor, N.Y.

Martens, J. W. M., G. Honee, D. Zuidema, J. W. M. van Lent, B. Visser, J. M. Vlak (1990) *Appl. Environmental Microbiol.* 56(9):2764–2770.

Merryweather, A. T., U. Weyer, M. P. G. Harris, M. Hirst, T. Booth, R. D. Possee (1990) *J. Gen. Virol.* 71:1535–1544.

Prefontaine, G., P. Fast, P. C. K. Lau, M. A. Hefford, Z. Hanna, R. Brosseau (1987) *Appl. Environ. Microbiol.* 53(12):2808–2814.

Prichard, R. K. et al. (1980) "The problem of anthelmintic resistance in nematodes," *Austr. Vet. J.* 56:239–251.

Sanger et al. [1977] *Proc. Natl. Acad. Sci. USA* 74:5463–5467.

Schnepf, H. E., H. R. Whiteley (1981) *Proc. Natl. Acad. Sci. USA* 78:2893–2897.

---

We claim:

1. A purified or isolated nematode-active toxin encoded by a polynucleotide sequence obtainable from *Bacillus thuringiensis* isolate PS80JJ1.

2. The nematode-active toxin, according to claim 1, wherein said toxin comprises an amino acid sequence shown in SEQ ID NO.4 or a nematode-active fragment thereof.

3. The nematode-active toxin, according to claim 1, wherein said toxin comprises an amino acid sequence shown in SEQ ID NO.4.

* * * * *

UNITED STATES PATENT AND TRADEMARK OFFICE
CERTIFICATE OF CORRECTION

PATENT NO.    : 5,959,080
DATED         : September 28, 1999
INVENTOR(S)   : Jewel Payne, Kenneth E. Narva, Jenny Fu It is certified that error appears in the above-identified patent and that said Letters Patent is hereby corrected as shown below:

Title page,
Item [57], ABSTRACT,
Line 1, "Noven" should read -- Novel --.

Column 2,
Line 65, "Figure 1 is a photograph" should read -- Figures 1A and 1B are photographs --.

Signed and Sealed this

Twelfth Day of February, 2002

*Attest:*

*Attesting Officer*

JAMES E. ROGAN
*Director of the United States Patent and Trademark Office*